(12) United States Patent
Pickett

(10) Patent No.: US 8,380,306 B2
(45) Date of Patent: Feb. 19, 2013

(54) IMPLANTABLE ELECTRODE

(75) Inventor: Christopher John Pickett, Norfolk (GB)

(73) Assignee: Biotectix, LLC, Boston, MA (US)

( * ) Notice: Subject to any disclaimer, the term of this patent is extended or adjusted under 35 U.S.C. 154(b) by 0 days.

(21) Appl. No.: 13/193,866

(22) Filed: Jul. 29, 2011

(65) Prior Publication Data

US 2012/0029585 A1 Feb. 2, 2012

(30) Foreign Application Priority Data

Jul. 29, 2010 (GB) .................................. 1012808.0

(51) Int. Cl.
*A61N 1/00* (2006.01)

(52) U.S. Cl. ........................................................... 607/5

(58) Field of Classification Search ........................ 607/5
See application file for complete search history.

(56) References Cited

U.S. PATENT DOCUMENTS

| | | | |
|---|---|---|---|
| 4,602,637 A | 7/1986 | Elmqvist et al. | |
| 4,762,136 A | 8/1988 | Baker, Jr. | |
| 5,080,099 A | 1/1992 | Way et al. | |
| 5,683,443 A | 11/1997 | Munshi et al. | |
| 7,421,299 B2 | 9/2008 | Frericks et al. | |
| 7,899,552 B2* | 3/2011 | Atanasoska et al. | 607/122 |
| 2001/0002000 A1 | 5/2001 | Kumar et al. | |
| 2004/0133258 A1 | 7/2004 | Frericks et al. | |
| 2011/0002000 A1 | 1/2011 | Tomaru | |
| 2011/0257504 A1* | 10/2011 | Hendricks et al. | 600/395 |

FOREIGN PATENT DOCUMENTS

| | | |
|---|---|---|
| DE | 3300672 | 7/1984 |
| EP | 0115778 | 8/1984 |
| EP | 0116280 | 8/1984 |
| EP | 0117972 | 9/1984 |
| WO | 8705814 | 10/1987 |
| WO | 9833552 | 8/1998 |
| WO | 2008033546 | 3/2008 |
| WO | 2008139200 | 11/2008 |
| WO | 2010059305 | 5/2010 |

OTHER PUBLICATIONS

Pickett, C.J., et al, "Synthesis and Anodic Polymerisation of an L-Cystine derivatised Pyrrole; Coplymerisation with a Tetraalkylammonium Pyrrole allows Reduction of the Cystinyl Film to a Cysteinyl State that Binds Electroactive $|Fe_4S_4|^{2+}$ Centres", Chem Soc., Chem Community, 1992, pp. 694-697.

Pickett, C.J., et al, "Iron-Sulfur Clusters in Ionic Polymers on Electrodes", J Chem. Soc., Dalton Trans., 1993, pp. 3695-3703.

Moutet, Jean-Claude et al., "Iron-Sulphur Clusters in Ionic Polymers on Electrodes", J. Chem. Soc., Chem. Community, 1989, pp. 188-190.

(Continued)

*Primary Examiner* — George Manuel
(74) *Attorney, Agent, or Firm* — Senniger Powers LLP

(57) ABSTRACT

An implantable electrode, for an implantable tissue stimulator, has an electrically conductive porous material comprising metal carbide, metal nitride, metal carbonitride, metal oxide or metal oxynitride and one or more coating layers on a surface thereof. The coating layer or at least one of the coating layers, is for contact with body tissue when the electrode is implanted. Each coating layer is an electrically conductive layer of polymer having a polypyrrole polymeric backbone or polythiophene polymeric backbone. The coating layer or layers are formed in situ by electropolymerisation. The polypyrrole or polythiophene may be substituted. The coating layer or layers can provide high charge storage capacitance and a fast discharging profile, as well as biocompatibility.

38 Claims, 1 Drawing Sheet

OTHER PUBLICATIONS

Pickett, Christopher J. et al., "Bioinorganic Reaction Centres on Electrodes. Modified Electrodes possessing Amino Acid, Peptide and Ferredoxin-type Groups on a Poly(pyrrole) backbone", J. Chem. Soc., Dalton Trans., 1994, pp. 2181-2189.

Ibrahim, S.K. et al, "Peptide derivatised poly(pyrrole) modified electrodes with built-in ion-exchange functions," Journal of Electroanalytical Chemistry 387 (1995) pp. 139-142.

Search Report from Great Britain Application No. GB1012808.0 date of search Oct. 6, 2010, 2 pages.

Riedmuller, J., et al. "Improvement of Stimulation and Sending Performance of Bipolar Pacemaker Leads", Proceedings of the Annual International Conference of the IEEE/EMBS, pp. 2364-2365 (1992).

Earley, S.T. et al., "Formation of adherent polypyrrole coating on Ti and Ti-6A1-4V alloy", Synthetic Metals 148(2), pp. 111-118, 2005, XP025271049; ISSN 0379-6779.

\* cited by examiner

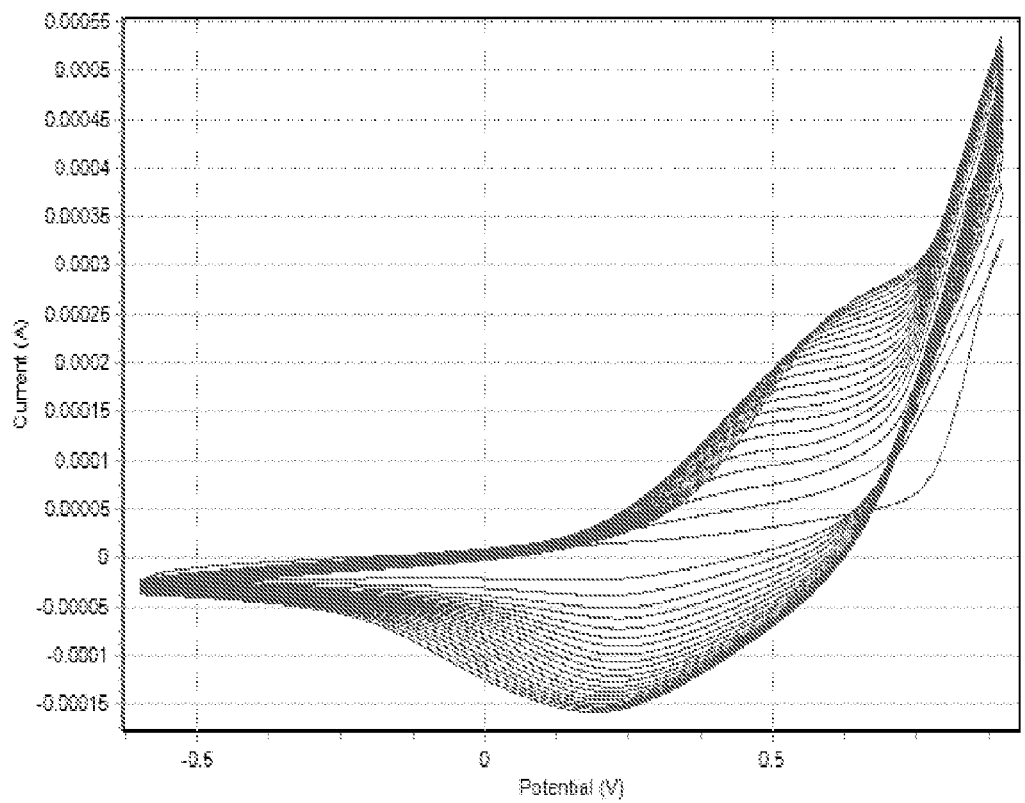

IMPLANTABLE ELECTRODE

FIELD OF THE INVENTION

This invention relates to an implantable electrode suitable for contact with body tissue when implanted in a human or other animal, especially a mammal, and to an implantable tissue stimulator having such an electrode, as well as to a method of making such an electrode.

BACKGROUND OF THE INVENTION

In most cases, implantable stimulation or stimulating electrodes, for example for heart pacemakers, consist of an electrode body having an insulated cable lead and an electrode head for the transmission of the stimulation pulses, i.e. the active or effective area of the electrode.

Such electrode materials should be compatible with the body, i.e. the formation of connective tissue layers should be very low if it is not suppressed altogether; in any case, the thickness of connective tissue should remain below 100 μm. The stimulation threshold, further, should be as constant as possible. Furthermore, a high double layer capacitance should form at the phase boundary of the electrode and bodily fluid, so that the polarization rise during the stimulation pulses are small, typically less than 0.1V. The high double layer capacitance that is sought has a beneficial effect in the case of stimulation electrodes because, as a result of the impressed current, only slight potential changes occur, electrochemical reactions with the bodily fluid are largely suppressed and the energy outlay is slight.

The demands noted above have been partially met by electrodes in which the electrode head consists of glassy carbon. A high double layer capacitance is achieved by means of an activation of the surface of the glassy carbon, whereby a thin, firmly adhering layer of activated carbon is obtained, i.e. a surface with a microporous structure. Importantly, activated carbon also exhibits good biocompatibility.

However, mechanical processing (during manufacture) and electrical contacting in such a device have proven problematic. This has led to the development of pacing materials based on porous titanium nitride and other nitride or carbide materials which are conducting and have high intrinsic surface areas which meet the capacitance and energy needs of a stimulator.

Published US patent application 2001/0002000 A1 discloses substrates of plastic, metals, etc., with a biocompatible coating, which is formed from amorphous titanium nitride. The applications of the substrates are in the field of cardiac pacemakers and electrodes. European published patent applications EP 0 117 972 A, EP 0 116 280 A and EP 0 115 778 A disclose electrodes for medical applications, provided with porous layers of titanium nitride. U.S. Pat. No. 4,602,637 discloses a cardiac pacemaker system in which the passive electrode is coated, for example, with activated carbon or titanium nitride. German published patent application DE 33 00 672 A1 discloses a cardiac pacemaker system with an electrode which has, for example, a coating of titanium nitride. The publication, J. Riedmüller, A. Bolz, H. Rebling, M. Schaldach, "Improvement of Stimulation and Sensing Performance of Bipolar Pacemaker Leads", Proceedings of the Annual International Conference of the IEEE/EMBS, pp. 2364-2365 (1992), discloses that the use of titanium nitride layers with anodic polarization leads to the formation of oxide layers in the region of the electrode surface. While the physical properties of the titanium nitride are substantially unchanged in stimulation electrodes with a titanium nitride layer which is used as the cathode, this is not the case with use as an anode. The attack by OH-ions leads to the formation of oxide layers, which cause a rise of impedance and therewith also a rise of the threshold voltage.

U.S. Pat. No. 4,762,136 describes electrodes for use in cardiac pacing having a surface layer of iridium oxide overlying a substrate. U.S. Pat. No. 5,683,443 likewise describes iridium oxide as a non-native coating on a metal electrode surface, and also mentions mixtures of oxides such as ruthenium oxide, iridium oxide and tantalum oxide.

U.S. Pat. No. 5,080,099 describes the use of conductive polymeric hydrogels as a surface layer of an electrode intended to be applied to a patient's skin for exterior stimulation of the heart.

Use of functionalized polypyrrole layers on electrodes and other implantable devices is known for example from WO98/33552 and WO2008/139200. The latter discloses stents having layers which provide good biocompatibility and anti-thrombolytic properties.

WO2008/033546 describes use of polyoxometalates in a surface layer of an implantable electrode, where the layer may be a conductive polymer, and is discussed more below.

SUMMARY OF THE INVENTION

The present inventor has appreciated that the porous conducting interface of an implantable electrode can be adapted to improve its charge capacitance. Further advantage may be provided if the porous conducting interface is biocompatible, thereby causing minimal tissue irritations after implantation, and also has an anti-inflammatory effect. Furthermore, the titanium nitride or other material should be resistant to corrosion, particularly under pulse regimes where hydroxide is generated.

The present invention provides thin conducting coatings which can be deposited on high surface area materials such as titanium nitride and which (i) possess tissue biocompatibility, (ii) can be anti-inflammatory, (iii) can provide stability to body fluids and prevent base generation, (iv) can retain or enhance capacitance and have low impedance characteristics, (v) can strongly adhere under in vivo pulsing conditions.

This invention can provide strongly adherent thin films based on poly(pyrroles) which can be grown upon titanium nitride and related nitride, carbide or oxide materials and which may possess a high degree of biocompatibility and other desirable properties such as those cited above.

According to the invention there is provided an implantable electrode having an electrically conductive porous material comprising metal carbide, metal nitride, metal carbonitride, metal oxide or metal oxynitride and one or more coating layers on a surface thereof, the coating layer or at least one of the coating layers being for contact with body tissue when the electrode is implanted and each coating layer being an electrically conductive layer of polymer having a polypyrrole polymeric backbone or polythiophene polymeric backbone.

In one embodiment of the invention, the electrically conductive porous material comprises metal carbide, metal nitride or metal carbonitride.

Preferably the or each coating layer is one formed in situ by electropolymerisation of pyrrole, a pyrrole derivative monomer, thiophene or a thiophene derivative monomer.

Preferably the coating layer is a polypyrrole derivative in the form of polypyrrole substituted at the 1 or 3 position. The 1 position is at the N atom. There are two 3 positions. Substitution may be at one or both of the 3 positions. In the case of thiophene, substitution is at one or both of the 3 positions. Preferably the substituent increases adhesion of the coating layer to the metal carbide or metal nitride material and/or increases tissue compatibility of the coating layer, relative to the adhesion or tissue compatibility of polypyrrole or polythiophene respectively.

In the case of a substituent at the 1 position of pyrrole, the substituent group preferably has the structure

-A-X where A is alkyl or alkenyl having 1-6 C atoms, preferably 1-3 C atoms, preferably unbranched, and optionally substituted, and where X is selected from
- —COOH or —COO$^-$
- —COOR'
- —CONH$_2$
- —CONHR'
- —CON(R')$_2$
- —COR'
- —F, —Cl, —Br, —I
- —CN
- —NO$_2$
- —OH
- —OR'
- —SH
- —SR'
- —O—CO—R'
- —NH$_2$
- —NHR'
- —NH(R')$_2$
- —N(R')$_3^+$ e.g. (N(CH$_3$)$_3$)$^+$
- —NH—CO—R'
- —NH—CO—H
- —NR'—CO—R'
- —NR'—SO$_2$H
- —NR'—SO$_2$R'
- —SO$_2$R'
- —OSO$_2$R' and
- —OPO$_3$, wherein R' is alkyl or alkenyl of 1 to 6 C atoms, preferably 1 to 4 C atoms.

A is preferably unsubstituted, but optionally is substituted by any of
- —COOH or —COO$^-$
- —COOR'
- —CONH$_2$
- —CONHR'
- —CON(R')$_2$
- —COR'
- —F, —Cl, —Br, —I
- —CN
- —NO$_2$
- —OH
- —OR'
- —SH
- —SR'
- —O—CO—R'
- —NH$_2$
- —NHR'
- —NH(R')$_2$
- —N(R')$_3^+$ e.g. (N(CH$_3$)$_3$)$^+$
- —NH—CO—R'
- —NH—CO—H
- —NR'—CO—R'
- —NR'—SO$_2$H
- —NR'—SO$_2$R'
- —SO$_2$R'
- —OSO$_2$R', and
- —OPO$_3$, wherein R' is alkyl or alkenyl of 1 to 6 C atoms, preferably 1 to 4 C atoms.

In the case of a substituent at the 3 position of pyrrole or thiophene, the substituent group preferably has the structure
- —X or
- -A-X where A (if present) and X are as defined above.

In the above defined substituents, preferably X is selected from
- —COOH or —COO$^-$
- —COOR'
- —Cl
- —SH, and
- —OPO$_3$.

Particularly, X may be —COOH or COO$^-$.

The substituents —COOH, —COO$^-$ and —SH particularly confer good adhesive properties to the coating layer.

Alternatively the substituent at the 1 or 3 position of pyrrole or the 3 position of thiophene may be an allyl-terminated pendent group as disclosed in WO2008/139200. Layers formed of such polymers are non-inflammatory in contact with body tissue. Thus, the allyl-terminated pendent group comprises a moiety selected from
- —O—CH$_2$—CH=CH$_2$
- —S—CH$_2$—CH=CH$_2$
- —S(=O)—CH$_2$—CH=CH$_2$
- —Se—CH$_2$—CH=CH$_2$ and
- —Se(=O)—CH$_2$—CH=CH$_2$.

Preferably the group comprises a moiety selected from
- —C(=O)—O—CH$_2$—CH=CH$_2$
- —CH$_2$—S(=O)—CH$_2$—CH=CH$_2$
- —S—S—CH$_2$—CH=CH$_2$
- —S(=O)—S—CH$_2$—CH=CH$_2$ and
- —S—S(=O)—CH$_2$—CH=CH$_2$.

The pendent group may be bound to the pyrrole or thiophene ring via an amido, ester or ether moiety.

A monomer for forming a polymer coating containing such an allyl-terminated pendent group may be one defined as

A*-B-C-D-E where:

A* is the polymerisable component, particularly a pyrrole ring or a thiophene ring;

B is C$_{1-20}$ alkyl chain, which may be branched or unbranched, and optionally substituted;

C is amido (—CO—NH—), ester (—CO—O—) or ether (—O—), preferably amido;

D is C$_{1-20}$alkyl chain, which may be branched or unbranched, and optionally substituted; and E is the pendent group as described above.

Components B and D are each optional.

Components A*, B (if present), C, D (if present) and E are covalently attached as shown above. Components B (if present), C and D (if present) together are the covalent linker.

Preferred optional substituents on B and/or D, when present, are any of
- —COOH or —COO$^-$
- —COOR'
- —CONH$_2$
- —CONHR'
- —CON(R')$_2$
- —COR'
- —F, —Cl, —Br, —I
- —CN
- —NO$_2$
- —OH
- —OR'

—SH
—SR'
—O—CO—R'
—NH$_2$
—NHR'
—NH(R)$_2$
—N(R')$_3^+$ e.g. (N(CH$_3$)$_3^+$
—NH—CO—R'
—NH—CO—H
—NR'—CO—R'
—NR'—SO$_2$H
—NR'—SO$_2$R'
—SO$_2$R'
—OSO$_2$R'
—OPO$_3$
—C$_{5-20}$aryl
—C$_{1-7}$alkyl-C$_{5-20}$aryl, and
—C$_{1-7}$alkenyl-C$_{5-20}$aryl,
wherein R' is alkyl or alkenyl of 1 to 6 C atoms, preferably 1 to 4 C atoms.

As noted above, WO2008/033546 describes implantable electrodes in which the electrode surface may be conductive ceramics having an electrode surface having a polyoxometalate (POM). The POM may be in a film of conductive polymer formed onto the electrode surface. Among conductive polymers, poly(pyrrole)s and poly(thiophene)s are mentioned. Accordingly in one form of definition of the present invention, the use of a coating layer which is an electrically conductive layer selected from poly(pyrrole)s and poly(thiophene)s and containing one or more polyoxometalates is specifically excluded. Particularly, use of a coating layer which is an electrically conductive layer of polymer having a polypyrrole polymeric backbone or polythiophene polymeric backbone and containing one or more polyoxometalates may be specifically excluded.

Preferably the or each of the coating layer(s) of polymer in the electrode of the invention is free of non-exchangeable and/or non-mobile anions, such as polyoxometalates, which are extraneous to the polymer. By a non-exchangeable or non-mobile anion is meant an anion which is entrapped or otherwise non-mobile in the layer and cannot take part in charging/discharging processes. The absence of such non-exchangeable and non-mobile anions, which are extraneous for example in that they are not covalently bound to the polypyrrole/polythiophene polymer, will avoid limitation of the ability for rapid charging and discharging with movement of counterions.

The metal of the metal carbide, metal nitride, metal carbonitride, metal oxide or metal oxynitride of the electrically conductive porous material may be any which forms an electrically conductive carbide, nitride, carbonitride, oxide or oxynitride and particularly an electrically conductive carbide, nitride, carbonitride, oxide or oxynitride which is not soluble in human body tissue and fluid, particularly blood. Preferred examples of such metals are Ti, Zr, V, Nb, Ta, Ir, Ru, Mo, Hf and W. Mn and Ni are other examples. Examples of suitable nitrides are TiN, ZrN, TaN, WN and Mo$_2$N. Examples of suitable carbides are TiC, ZrC, TaC, MoC and WC. An example of a suitable carbonitride is Ti(C,N). Examples of suitable oxides are RuO$_2$, IrO$_2$, NiO, MnO$_2$ and VO$_x$. An example of a suitable oxynitride is TiO$_x$N$_y$. The carbides, nitrides, carbonitrides, oxides and oxynitrides employed may be, and often are, non-stoichiometric, and thus may be expressed for example as MN$_x$, MO$_x$, MC$_x$, where M is the metal, e.g. WC$_x$, IrO$_x$, RuO$_x$. More than one metal may be present in the carbide/nitride/carbonitride/oxide, examples being TiO$_2$—IrO$_2$, IrO$_2$—TaO$_2$, (Ti, Zr)N. An example of a suitable mixed oxide of two metals is indium-tin oxide (ITO), which is well known as providing a transparent electrode surface.

The electrical conductivity of the metal carbide, nitride, carbonitride oxide and oxynitride materials employed in the invention may range from high conductivity to low conductivity. Some of the suitable materials here listed may be classed as semiconductors, but provide sufficient conductivity. The material may be doped to provide suitable conductivity. Typically the material has a volume resistivity at 20° C. of not more than $1 \times 10^8$ Ω·m, preferably not more than $1 \times 10^7$ Ω·m. Important is the ability of the material, as a coating on an electrode, to increase the charge injection capacity and/or reduce the polarization of the electrode.

Where metal carbide, nitride or carbonitride is employed, the metal is preferably selected from Ti, Zr and Ta. Preferably the metal carbide or metal nitride is selected from TiC, TiN, ZrC, ZrN, TaC, TaN. A metal carbonitride such as Ti(C,N) may be employed.

Preferably the porous material is supported on a metallic base body.

Preferably the or each coating layer has a thickness in the range from a molecular monolayer to 10 μm, more preferably 0.01 μm to 1 μm. There may be at least two of the coating layers which have respectively different substituted pyrrole monomeric units or different substituted thiophene monomeric units conferring respectively different properties to the electrode.

The coating layer is formed directly on the conductive porous material. There may be plural coating layers, formed successively one on another, the first being directly on the conductive porous material.

There may be plural layers of the conductive porous material, for example of different chemical composition.

Preferably the coating layer completely covers the conductive porous material and a metallic base body (if provided) so that the porous material and the metallic base body do not contact body tissue on implantation of the electrode.

Typically in the invention the electrode is comprised of an electrically conductive carrier material, e.g. a metal base body, which has a porous layer consisting of or including a carbide, a nitride, a carbonitride, an oxide or an oxynitride of at least one of the metals titanium, vanadium, zirconium, niobium, molybdenum, hafnium, tantalum or tungsten in its active region. The active region should thereby at least partially exhibit such a porous layer. Upon this porous conductor a thin film, preferably not more than 1 μm in thickness, of the conducting polymer, is typically grown from the monomer electrochemically.

This invention can thus provide:
(i) protection of the underlying porous structure, for example TiN, from hydrolytic attack by hydroxide,
(ii) provision of biocompatible and anti-inflammatory surfaces,
(iii) enhanced capacitance and low impedance.

Implantable electrodes for the stimulation of bodily tissue, particularly for use in pacemakers, defibrillators, and bone stimulators or neurostimulators, are known in manifold forms. The great majority of stimulation electrodes of this type are based on metallic materials, since these are predestined for the transmission of electrical currents to living tissue because of their good conductivity. The invention is applicable to such devices.

High electrode capacitance and therefore low electrode impedance and a high degree of biocompatibility are of importance for the usage value of an implantable stimulation electrode, particularly one which is intended for long-term use on a tissue stimulator having an exhaustible energy source and which therefore must contribute to the minimal energy consumption.

As mentioned above it is known that poly(pyrroles) can possess high biocompatibility and can display anti-thrombolytic behavior. The same is believed to be true for poly (thiophenes). Their bulk properties can be tailored to minimize water ingress to the porous layer which can otherwise lead to corrosion of the nitride or carbide by oxide formation.

The pore system of the porous layer in combination with the thin conducting pyrrole or thiophene polymer film provides a high double layer capacitance which is advantageous in use as stimulation electrodes of implantable heart pacemakers and other devices, to obtain low energy requirement.

Infection associated with implantation of medical devices is a serious health and economic concern. When infection associated with an implanted medical device does occur, explanting (removing) the device is often the only appropriate course of action. The conducting thin film provides a therapeutic vehicle for covalent binding of anti-infective agents.

The invention also provides an implantable tissue stimulator having an implantable electrode of the invention as described above. Typically such an implantable tissue stimulator has electrical power supply means and means for applying electrical stimulation pulses to the electrode using electrical power from the power supply means. The power supply means may be electrical power storage means such as a battery, and/or means for receiving electrical power transmitted from outside the body, e.g. by radio frequency coupling.

The implantable tissue stimulator may for example be a pacemaker, a defibrillator, a bone stimulator or a neuro-stimulator.

The invention further consists in a method of making an implantable electrode of the invention as described above, including the step of electropolymerizing pyrrole, a substituted pyrrole, thiophene or a substituted thiophene in situ on the metal carbide, metal nitride, metal carbonitride, metal oxide or metal oxynitride material. Techniques for this procedure of electropolymerisation are known and are described in the prior art documents discussed above. They apply to thiophene as well as to pyrrole. The polymer may be converted after deposition by electropolymerisation, by reacting the electropolymerized polypyrrole, substituted polypyrrole, thiophene or substituted polythiophene to add a substituent or change the substituent.

DRAWINGS

FIG. 1 is a cyclic voltammogram of one example of a method of making an electrode of the invention.

EXAMPLES

Coating of Titanium Nitride Substrates

Electrochemical procedures were used to deposit pyrrole polymers onto porous TiN electrodes. The electrodes were dome shaped with approximate dimensions: height 1 mm, diameter 1.2 mm, area 4.3 mm$^2$. Electrochemical coating upon two types of TiN deposit were established. The two types of TiN electrodes have TiN layers formed by PACT (plasma assisted coating technology) TiN and HSA (high surface area) TiN.

Electrodes were first cleaned by sonicating in 1% Micro90 solution (aq) (a cleaning solution) for 1 minute then washed in a flowing stream of DI water (deionized water) for 30 seconds, then blown dry with nitrogen and used immediately. Electrodeposition was performed in a one compartment cell with lead as working electrode, Ag/Ag$^+$ (non aqueous) as reference electrode and stainless steel as counter electrode (25×75 mm) looped around inner surface of cell. Electrolyte solution was degassed with bubbling nitrogen for 30 minutes and kept under a nitrogen blanket during the experiment. After electrodeposition was performed, the electrodes were washed with acetonitrile and blown dry with nitrogen.

For all these experiments, films were left in the oxidized (conducting) state and the thicknesses were approximately 0.5-1 μm (the actual amount is proportional to charge passed).

Reference Electrode:

Ag/AgCl (non aqueous)

Electrodeposition Technique:

CA—chronoamperometry

CV—cyclic voltammetry

Solvent:

MeCN—acetonitrile (dried, distilled)

Electrolyte:

TBA—tetrabutylammonium cation

BF4—tetrafluoroborate anion

Monomer: 3-pyrrol-1-yl propanoic acid (monomer A below)

Shiny black films of monomer A were successfully deposited on four TiN electrodes (TiN is matt black before deposition) by CV and CA methods, see the Table below.

The cyclic voltammetric behavior of electrodeposition of polymer of monomer A on TiN exhibited behavior similar to that observed on Pt electrodes. Polymer redox peak sizes increased with each cycle suggesting good deposition behavior as shown in FIG. 1.

TABLE

| Sample No. | Material | monomer | electrolyte | solvent | voltammetry conditions |
| --- | --- | --- | --- | --- | --- |
| SR3-183-2 | Pulse PACT TiN | 10 mM A | 0.2M TBA BF4 | MeCN (dry) | CA +0.8 V, 600 seconds, 0.113 C |
| SR3-183-3 | Pulse PACT TiN | 10 mM A | 0.2M TBA BF4 | MeCN (dry) | i) CV −0.6→+0.9 V, 100 mV/sec, 20 cycles ii) CV −0.6→+0.9 V, 100 mV/sec, 20 cycles |

TABLE-continued

| Sample No. | Material | monomer | electrolyte | solvent | voltammetry conditions |
|---|---|---|---|---|---|
| SR3-183-4 | Pulse HSA TiN | 10 mM A | 0.2M TBA BF4 | MeCN (dry) | CV −0.6→+0.9 V, 100 mV/sec, 20 cycles |
| SR3-183-5 | Pulse HSA TiN | 10 mM A | 0.2M TBA BF4 | MeCN (dry) | CA +0.8 V, 300 seconds, 0.057 C |

FIG. 1 shows the growth of monomer A on a titanium nitride dome electrode. The growth of the polymer increases with each electrochemical cycle as evident from the increased current levels. The charge-discharge cycle shows high charge storage capacitance of the polymer film between 0 and 0.7V, which is highly suitable for a cardiac stimulation electrode.

This charge storage capacity of the polymer film is a beneficial property for the safe and efficient use of the electrode when implanted. The polymer film is capable of charge/discharge cycles by oxidation/reduction (removal/addition of electrons) as well as by charging/discharging of double layer capacitance. The cyclic voltammogram of FIG. 1 shows that the addition of monomer A increases the reversible charge storage and delivery capacity of the electrode. It also shows a fast discharging profile.

Electron microscopy has shown that the films having polypyrrole backbone produced in these examples have good film morphology, with good surface coverage, no cracks and no de-lamination.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

What is claimed is:

1. An implantable electrode having an electrically conductive porous material comprising metal carbide, metal nitride, metal carbonitride, metal oxide or metal oxynitride and one or more coating layers on a surface of said material, said coating layer or at least one of said coating layers being for contact with body tissue when the electrode is implanted, and each said coating layer being an electrically conductive layer of polymer having a polypyrrole polymeric backbone or polythiophene polypyrrole substituted at the 1-position (N-atom) or the 3-position with a substituent —A-X or an allyl-terminated pendent group, or is a polythiophene substituted at the 3-position with a substituent —X, —A-X, or an allyl-terminated pendent group, wherein:

A is alkylene or alkenylene of 1-6 carbon atoms;
   X is —COOH, —COO⁻, —COOR', —CONH₂, —CONHR', —CON(R')₂, —COR', —F, —Cl, —Br, —I, —CN, —NO₂, —OH, —OR', —SH, —SR', —O-CO-R', —NH₂, —NHR', —NH(R')₂, —N(R')₃⁺, —NH-CO-R', —NH-CO-H, —NR'-CO-R', —NR'-SO₂H, —NR'-SO₂R', —SO₂R', —OSO₂R' or —OPO;
   R' is alkyl or alkenyl of 1-6 carbon atoms; and
   the allyl-terminated pendent group comprises —O-CH₂-CH=CH₂, —S-CH₂- CH=CH₂, —S(=O)-CH₂-CH=CH₂, —Se-CH₂-CH=CH₂, or —Se(=O)-CH₂-CH=CH₂.

2. An implantable electrode according to claim 1, wherein the at least one said coating layer is a polypyrrole derivative in the form of polypyrrole substituted at the 1-position (N-atom) and the 3-position.

3. An implantable electrode according to claim 1, wherein the electrically conductive porous material comprises metal carbide, metal nitride or metal carbonitride.

4. An implantable electrode according to claim 3, wherein the metal carbide, metal nitride or metal carbonitride is TiC, TiN, ZrC, ZrN, TaC, TaN or Ti(C,N).

5. An implantable tissue stimulator having an electrode according to claim 3.

6. An implantable tissue stimulator according to claim 5, having electrical power supply means and means for applying electrical stimulation pulses to the electrode using electrical power from the power supply means.

7. An implantable tissue stimulator according to claim 5, which is a pacemaker, a defibrillator, a bone stimulator or a neuro-stimulator.

8. An implantable electrode according to claim 1, wherein the porous material is supported on a metallic base body, and the coating layer has a thickness in the range from a molecular monolayer to 10 µm.

9. An implantable electrode according to claim 8, wherein the coating layer has a thickness in the range from 0.01 µm to 1 µm.

10. An implantable electrode according to claim 1, having at least two said coating layers which have respectively different substituted pyrrole monomeric units or different substituted thiophene monomeric units.

11. An implantable electrode according to claim 1, wherein the or each said coating layer is free of non-exchangeable or non-mobile anions extraneous to said polymer.

12. An implantable tissue stimulator having an electrode according to claim 1.

13. An implantable tissue stimulator according to claim 12, having electrical power supply means and means for applying electrical stimulation pulses to the electrode using electrical power from the power supply means.

14. An implantable tissue stimulator according to claim 12, which is a pacemaker, a defibrillator, a bone stimulator or a neuro-stimulator.

15. A method of making an implantable electrode acording to claim 1, the method including the step of electropolymerizing pyrrole, a substituted pyrrole, thiophene or a substituted thiophene in situ on the electrically conductive porous material to form the coating layer as an electropolymerized polymer.

16. A method according to claim 15, including the step of reacting the electropolymerized polymer after polymerization to add a substituent or change the substituent.

17. A method according to claim 15, wherein the electrically conductive porous material comprises metal carbide, metal nitride or metal carbonitride.

18. An implantable electrode according to claim 1, wherein the substituent is —A-X and A is alkylene or alkenylene having 1-3 carbon atoms.

19. An implantable electrode according to claim 1, wherein the substituent is —A-X and A is unbranched alkylene or unbranched alkenylene.

20. An implantable electrode according to claim 1, wherein the substituent is —A-X and A is unsubstituted.

21. An implantable electrode according to claim 1, wherein the substituent is —A-X and A is substituted.

22. An implantable electrode according to claim 1, wherein the substituent is —A-X and A is substituted with —COOH, —COO⁻, —COOR', —CONH$_2$, —CONHR', —CON(R')$_2$, —COR', —F, —Cl, —Br, —I, —CN, —NO$_2$, —OH, —OR', —SH, —SR', —O-CO-R', —NH$_2$, —NHR', —NH(R')$_2$, —N(R')$_3^+$, —NH-CO-R', —NH-CO-H, —NR'-CO-R', —NR'-SO$_2$H, —NR'-SO$_2$R', —SO$_{2\ R'}$, —$_{OSO2}$R', or OPO$_3$ wherein R' is alkyl or alkenyl of 1-6 carbon atoms.

23. An implantable electrode according to claim 1, wherein R' of the substituent group is from 1-4 carbon atoms.

24. An implantable electrode according to claim 1, wherein X of the substituent group at the 3 position of pyrrole or thiophene is —COOH, —COO⁻, —COOR, —Cl, —SH, or —OPO$_3$.

25. An implantable electrode according to claim 1, wherein X of the substituent group at the 3 position of pyrrole or thiophene is —COOH or —COO⁻ or —SH.

26. An implantable electrode according to claim 1, wherein X of the substitutent group at the 3 position of pyrrole or thiophene is —COOH or —COO⁻.

27. An implantable electrode according to claim 1, wherein the polypyrrole or the polythiophene has an allyl-terminated pendent group comprising —C(=O)-O-CH$_2$-CH=CH$_2$, —S-S-CH$_2$-CH=CH$_2$, —S(=O)-S-CH$_2$-CH=CH$_2$, —CH$_2$-S(=O)-CH$_2$-CH=CH$_2$, or —S-S(=O)-CH$_2$-CH=CH$_2$.

28. An implantable electrode according to claim 1, wherein the polypyrrole or the polythiopene has an allyl-terminated pendent group bound to a pyrrole or a thiophene ring via an amido, ester or ether moiety.

29. An implantable electrode according to claim 1, wherein the polypyrrole or the polythiophene has an allyl-terminated pendent group and is derived from a monomer A*-B-C-D-E wherein:
A* is a pyrrole ring or a thiophene ring;
B is absent or C$_1$-C$_{20}$ alkylene;
C is —CO-NH—, —CO-O— or —O—;
D is absent or C$_1$-C$_{20}$ alkylene; and
E is the allyl-terminated pendent group.

30. An implantable electrode according to claim 29, wherein B or D is absent.

31. An implantable electrode according to claim 29, wherein B and D are absent.

32. An implantable electrode according to claim 29, wherein B or D is C$_1$-C$_{20}$ alkylene.

33. An implantable electrode according to claim 29, wherein B and D are C$_1$-C$_{20}$ alkylene.

34. An implantable electrode according to claim 29, wherein B or D are branched C$_1$-C$_{20}$ alkylene.

35. An implantable electrode according to claim 29, wherein B or D are unbranched C$_1$-C$_{20}$ alkylene.

36. An implantable electrode according to claim 29, wherein C is —CO-NH—.

37. An implantable electrode according to claim 29, wherein B or D is C$_1$-C$_{20}$ alkylene substituted with —COOH, —COO⁻, —COOR', —CONH$_2$, —CONHR', —CON(R')$_2$, —COR', —F, —Cl, —Br, —I, —CN, —NO$_2$, —OH, —OR', —SH, —SR', —O-CO-R', —NH$_2$, —NHR', —NH(R')$_2$, —N(R')$_3^+$, —NH-CO-R', —NH-CO-H, —NR'-CO-R', —NR'-SO$_2$H, —NR'-SO$_2$R', —SO$_{2\ R'}$, —$_{OSO2}$R', —OPO$_3$, —C$_5$—C$_{20}$ aryl, —C$_1$C$_7$ alkyl-C$_5$-C$_{20}$ aryl, or —C$_1$—C$_7$ alkenyl-C$_5$—C$_{20}$ aryl wherein R' is alkyl or alkenyl of 1-6 carbon atoms .

38. An implantable electrode according to claim 1, wherein the substituent is —X.

* * * * *